(12) United States Patent
Trainoff

(10) Patent No.: US 7,213,439 B2
(45) Date of Patent: May 8, 2007

(54) AUTOMATIC BRIDGE BALANCING MEANS AND METHOD FOR A CAPILLARY BRIDGE VISCOMETER

(75) Inventor: Steven P. Trainoff, Goleta, CA (US)

(73) Assignee: Wyatt Technology Corporation, Santa Barbara, CA (US)

(*) Notice: Subject to any disclaimer, the term of this patent is extended or adjusted under 35 U.S.C. 154(b) by 177 days.

(21) Appl. No.: 11/090,371

(22) Filed: Mar. 28, 2005

(65) Prior Publication Data
US 2006/0213256 A1 Sep. 28, 2006

(51) Int. Cl.
*G01N 11/08* (2006.01)
(52) U.S. Cl. .................... 73/1.02; 73/1.62; 73/1.88; 73/54.05; 73/54.09
(58) Field of Classification Search ............. 73/1.01, 73/1.02, 1.16, 1.25, 1.35, 1.57, 1.69, 1.73, 73/1.88, 54.01, 54.04, 54.05, 54.06, 54.09
See application file for complete search history.

(56) References Cited

U.S. PATENT DOCUMENTS

| | | | | |
|---|---|---|---|---|
| 2,449,067 | A * | 9/1948 | Guillemin, Jr. | 73/23.21 |
| 3,086,386 | A * | 4/1963 | Sixt | 73/23.2 |
| 3,808,877 | A * | 5/1974 | Blair | 73/54.06 |
| 4,384,472 | A * | 5/1983 | Tournier | 73/54.06 |
| 4,463,598 | A * | 8/1984 | Haney | 73/54.06 |
| 4,578,990 | A * | 4/1986 | Abbott et al. | 73/54.06 |
| 4,587,837 | A * | 5/1986 | Newbould | 73/54.04 |
| 5,756,883 | A * | 5/1998 | Forbes | 73/54.05 |
| 6,276,195 | B1 * | 8/2001 | de Corral | 73/54.04 |
| 6,877,361 | B2 * | 4/2005 | Bures | 73/54.04 |
| 6,948,508 | B2 * | 9/2005 | Shajii et al. | 137/1 |
| 2001/0013247 | A1 * | 8/2001 | Wilson et al. | 73/54.01 |

FOREIGN PATENT DOCUMENTS

| | | | |
|---|---|---|---|
| SU | 1116359 A | * | 9/1984 |
| SU | 1179151 A | * | 9/1985 |
| SU | 1571466 A | * | 6/1990 |

OTHER PUBLICATIONS

Waters et al., "Characterization of Hyaluronic Acid with On-Line Differential Viscometry, Multiangle Light Scattering, and Differential Refractometry", LCGC, Mar. 2005, pp. 1-5.*

* cited by examiner

*Primary Examiner*—Hezron Williams
*Assistant Examiner*—David A. Rogers
(74) *Attorney, Agent, or Firm*—Morland C. Fischer

(57) ABSTRACT

A thermally controlled stage is connected within one arm of a bridge of a capillary bridge viscometer so that the bridge can be balanced in situ to provide accurate measurement signals. The thermally controlled stage includes a tuning capillary tubing portion that is wrapped around a thermally conductive core. A resistance heater or a Peltier thermoelectric device is located in close proximity to the capillary tubing portion. The heater or Peltier device and the capillary tubing portion are located within a thermally insulated housing. The heater or Peltier device varies the temperature of the capillary tubing portion to cause a corresponding change in the flow impedance of the tuning capillary tubing portion of the arm of the bridge in which the thermally controlled stage is connected. The temperature of the tuning capillary tubing portion is monitored and adjusted until any pressure differential across the bridge is eliminated, whereby to trim in the balance of the bridge.

21 Claims, 4 Drawing Sheets

AUTOMATIC BRIDGE BALANCING MEANS AND METHOD FOR A CAPILLARY BRIDGE VISCOMETER

BACKGROUND OF THE INVENTION

1. Field of the Invention

This invention relates to a bridge balancing method and to a thermally controlled stage that is connected within one arm of a capillary bridge viscometer so that the temperature of the one arm can be controlled to a different temperature than the temperatures of the other three arms. This allows the bridge be automatically balanced to provide accurate measurement signals.

2. Background Art

An example of a capillary bridge viscometer which is adapted to accurately measure the specific viscosity of a solute in a suitable solvent is available by referring to U.S. Pat. No. 4,463,598 issued Aug. 7, 1984. Such a capillary bridge viscometer is useful in determining the molecular parameters of a polymer including molar mass and hydrodynamic radius. FIG. 1 of the drawings illustrates this well known capillary bridge viscometer.

The aforementioned patented differential viscometer includes a capillary bridge 50 that must be balanced to achieve accurate test results and a wide dynamic range. A solvent is usually supplied from a reservoir to the capillary bridge 50 by means of a low pulsation chromatography pump. Typically, the sensitivity of bridge 50 is limited by the pressure amplitude of the pump pulses. First and second capillaries 52 and 54 are connected in series between supply and discharge ports 60 and 62. Third and fourth capillaries 64 and 66 are connected in series between the supply and discharge ports 60 and 62. The series connected capillaries 52, 54, and 64, 66 are connected in parallel with one another between the supply and discharge ports 60 and 62 to form a fluid analog of the well known Wheatstone (i.e., resistance) bridge in the electrical art.

A delay volume 72 is located in the fluid arm of bridge 50 which contains the capillary 66. The delay volume 72 is constructed so as to have a negligible flow impedance, but a large internal volume. A differential pressure transducer 74 is connected in the capillary bridge 50 to measure the differential pressure across the bridge when different fluids are flowing through the capillaries thereof. Another differential transducer 75 is connected between the supply and discharge ports 60 and 62 to measure the pressure from the inlet to the outlet sides of the bridge. Typically, a zero reading of the pressure transducer 74 provides an indication that the bridge 50 is in balance.

In the traditional method for mechanically tuning the bridge 50, the length of one fluid arm of the bridge is changed by disassembling the bridge and precisely cutting off (or adding) a length of tubing. This is generally tedious and time consuming. Moreover, some fluid samples such as proteins, and the like, are known to stick to the fluid tubing which causes the original tuning to slowly drift with time. In this case, the fluid tubing must be cleaned out and flushed by the operator or a periodic rebalancing will otherwise be required. In the alternative, the viscometer will have to be returned to its manufacturer to be serviced. In either case, the viscometer will be rendered temporarily out of use with the consequence that fluid sample testing will be inefficiently delayed. What would be desirable is an improved balancing technique that is equivalent in effect to the mechanical balancing, but can be accomplished automatically and more accurately, as required, and without disassembly of the system.

SUMMARY OF THE INVENTION

Instead of varying the length of one fluid arm of a capillary bridge viscometer as has been accomplished in the past, an independently controlled thermal stage is connected within at least one arm of the bridge to achieve the desired balance. The thermal stage includes a tuning capillary tubing portion that is wrapped around a thermally conductive (e.g., brass or copper) core. The core and the tuning capillary tubing portion wrapped therearound are isolated from the other fluid arms of the bridge within an insulated thermal housing.

A (e.g. resistance) heater or a Peltier thermoelectric device is located within the thermal housing to lie in close thermal contact with the tuning capillary tubing portion. A temperature probe is also located within the housing so as to be responsive to the temperature of the capillary tubing portion. With the bridge of the capillary bridge viscometer initially out of balance, the power to the heater or Peltier device is adjusted to cause a change (i.e., either heating or cooling) in the temperature of the capillary tubing portion. As the temperature of the capillary rises or falls, the viscosity of the fluid in the capillary and the associated pressure drop across the fluid arm is correspondingly changed. Accordingly, the sum of the pressures in the fluid arm in which the tuning capillary tubing portion is connected is likewise changed. The temperature of the capillary tubing portion in the thermal housing of the thermally controlled stage is monitored until the pressure differential across the bridge is trimmed to 0, whereby the bridge will now be in balance so as to enable the viscometer to provide accurate measurement signals and the widest operating range. Once balanced, the temperature of the thermally controlled turning capillary is held constant.

DESCRIPTION OF THE PREFERRED EMBODIMENT

Disclosed herein is an automatic bridge balancing method and means for a capillary bridge viscometer. Viscosity is known to be a strong function of temperature. Therefore, it is contemplated to control the temperature of the fluid arms of the bridge viscometer to insure that the only pressure differences measured are due to changes in the composition of the sample rather than to thermally induced variations of the viscosity. The present improvement relies on using this strong temperature dependence as a tuning method.

Figure 1:
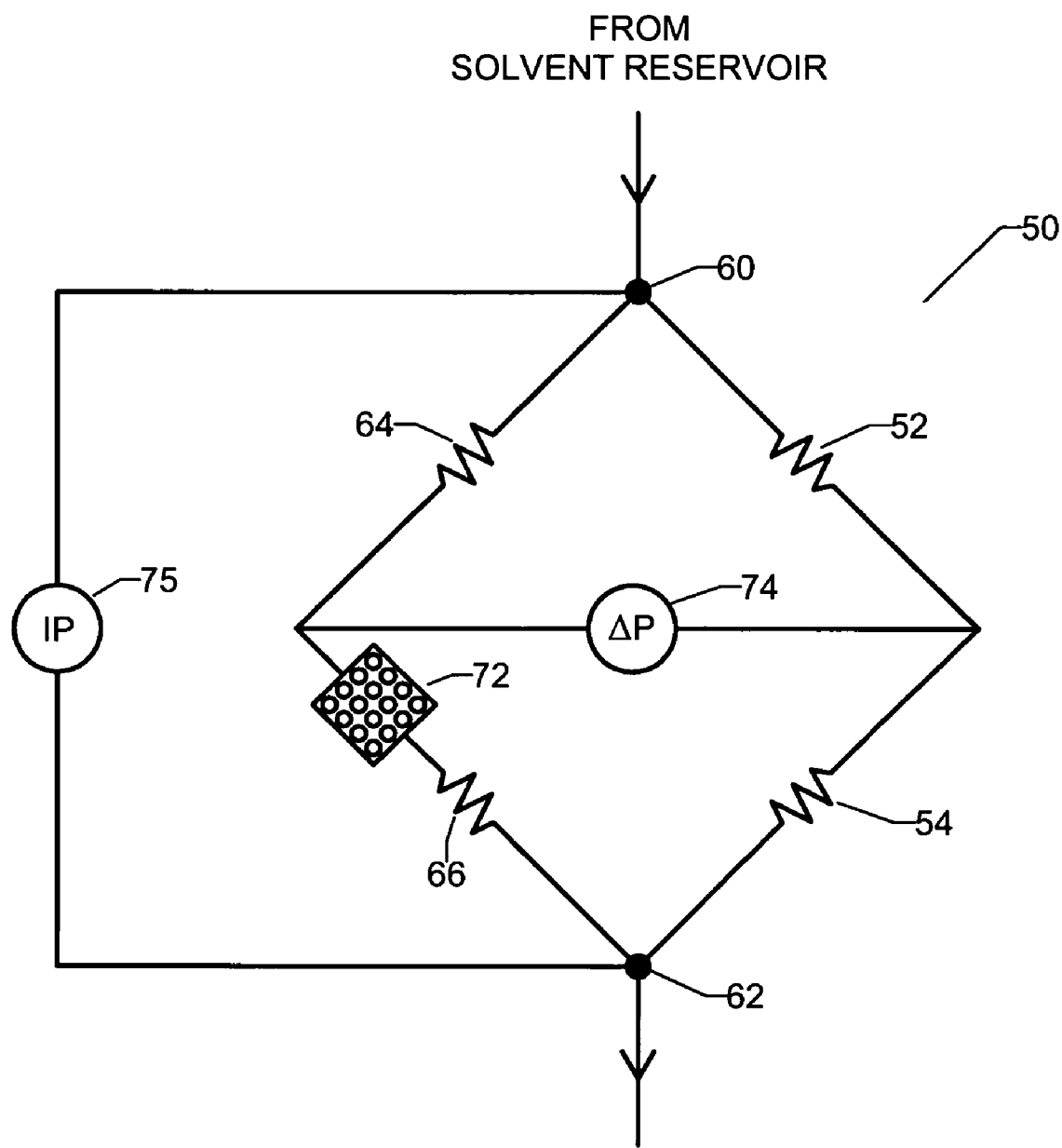
FIG. 1 shows a conventional bridge of the type that is common to a capillary bridge viscometer.

Rather than attempting to mechanically tune the bridge 50 of FIG. 1 while encountering the inconvenience and time delay associated with changing the length of one fluid arm thereof to constantly keep the bridge in balance, it has been discovered that the bridge may be balanced by heating or cooling the arm. More particularly, instead of adjusting the length of a fluid tubing line to tune the bridge, it has been found that a more efficient approach is to heat or cool one arm of the bridge, or a portion thereof, to achieve the desired balance.

Figure 2:
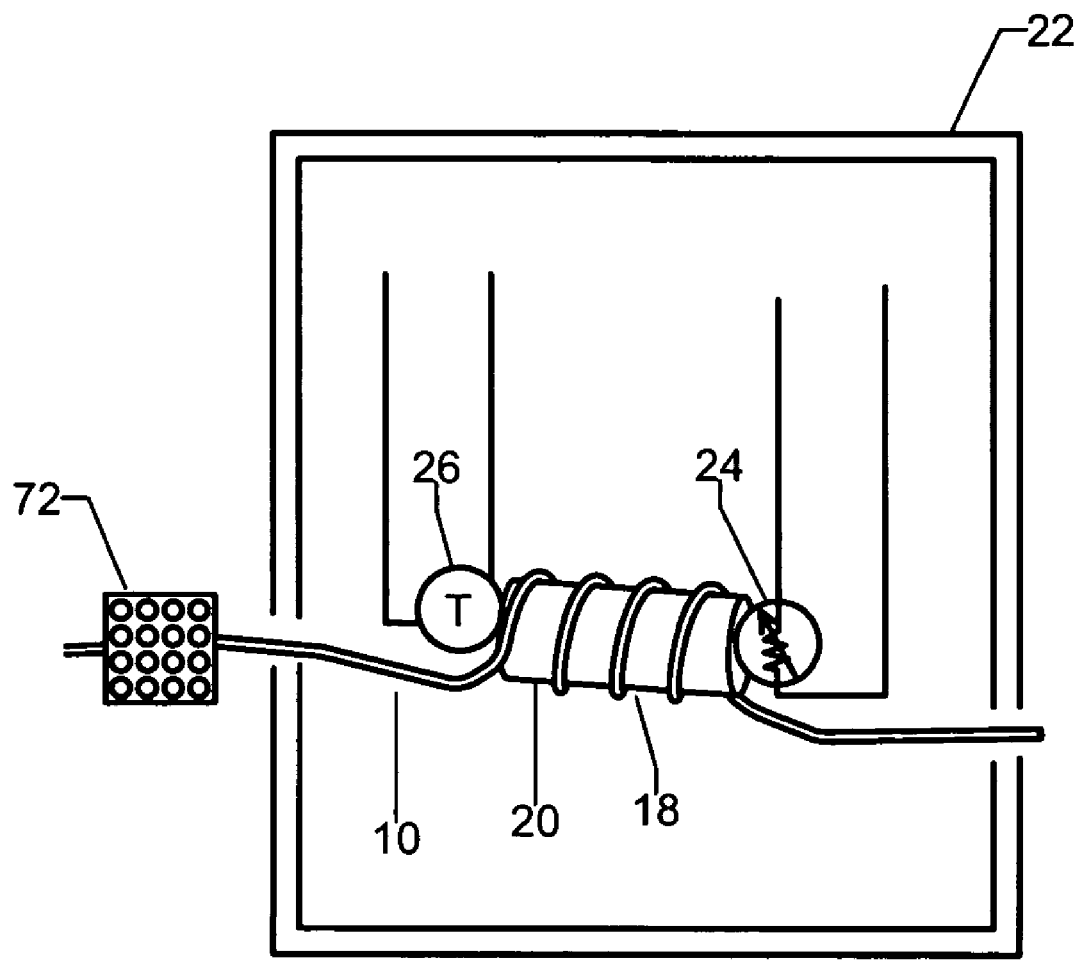
FIG. 2 shows details of a thermally controlled stage that is added to one arm of the bridge of FIG. 1 and that includes a heater to achieve an accurate and automatic balancing thereof.

Referring now to FIG. 2 of the drawings, there is shown one fluid tubing arm 10 of a capillary bridge viscometer that is to be substituted for the fluid tubing arm from the bridge 50 shown in FIG. 1 within which the aforementioned fluid sample delay volume 72 is connected. In accordance with the preferred improvement, the capillary tubing portion 66 of the bridge 50 of FIG. 1 is replaced by a thermally controlled stage containing a thermally tuned capillary tubing portion 18. The new capillary tubing portion 18 is manufactured from a thermally conductive material having a flow impedance. Capillary tubing portion 18 is wrapped around a thermally conductive (e.g., brass or copper) core 20 that is isolated from the other fluid tubing arms within a thermally insulated housing 22 of the thermally controlled stage. Although the core 20 is illustrated in FIG. 2 as a cylinder, it is to be understood that the core may have any other shape (e.g., a spool, cube, plane, etc.) that will facilitate the capillary tubing portion 18 being wrapped therearound and a soon to be described heating or cooling device being anchored thereto. In this same regard, while the preferred embodiment of the capillary tubing portion 18 is shown in FIG. 2 as a coil that is wound around the core 20, the capillary tubing portion 18 may have other suitable configurations so as to maximize its thermal contact with the core 20.

In the bridge balancing configuration and technique of FIG. 2, the tuning capillary tubing portion 18 is located downstream (i.e., closer to the discharge port 62 of the bridge) from the fluid sample delay volume 72. A (e.g., resistance) heater 24 is located within the thermal housing 22 of the thermally controlled stage so as to be anchored in close proximity to the core 20. A temperature probe 26 (e.g., a thermocouple) is also located within housing 22 so as to be responsive to the temperature of capillary tubing portion 18. It is preferable that temperature probe 26, like heater 24, be anchored in close proximity to the core 20 so as to be able to accurately measure the temperature of the capillary 18.

The measurement begins by establishing a flow of solvent though the viscometer bridge and waiting until the outputs of the bridge transducers (designated 74 and 75 in FIG. 1) become stable. Initially, the output of the differential pressure transducer 74 is usually not zero which indicates that the bridge is out of balance. This imbalance can be caused by small imperfections of construction or changes in the inner diameter of the tubing due to the contaminating effects of previous measurements. Alternatively, the bridge can be intentionally imbalanced during construction so that thermal balancing method herein disclosed may be used to controllably bring the bridge into balance.

Adjusting the power to the heater 24 varies the temperature of the tuning capillary tubing portion 18 in fluid arm 10 that is wrapped around core 20 within the thermal housing 22. As the temperature rises, the viscosity of the fluid flowing through the tuning capillary tubing portion 18 is correspondingly decreased, and the pressure drop across the arm 10 is correspondingly reduced. The bridge is brought into balance by monitoring the output of the differential pressure transducer 74 extending across the bridge 50 of FIG. 1. When the transducer 74 reads zero, the bridge in which the arm 10 is connected will be suitably balanced. The temperature measured by temperature probe 26 is then maintained constant by adjusting the output power of heater 24. The bridge 50 is now ready to receive one or more test samples. After the samples have fully exited the bridge, the system may be retuned, at the operator's discretion.

It will now be demonstrated that this method of balancing the bridge does not negatively impact the accuracy of the measurement. In the fluid analog of the Wheatstone bridge represented by FIG. 1, the non-turbulent mass flow through a capillary is given by Poiselle's law:

$$Q = \frac{\Delta p}{R\eta}, \quad (1)$$

where Q, is the mass flow rate though the each tube, $\Delta p$ is the pressure across the tube, $\eta$ is the viscosity of the fluid flowing through the tube, and R is the flow impedance of the tube defined by:

$$R = \frac{8l}{\pi r^4}, \quad (2)$$

where l is the length the tube and r is the inner radius of the tube. When connected in this configuration with all of the arms of bridge 50 having an identical flow impedance, the bridge viscometer measures the specific viscosity from measurements of the two differential transducers 74 and 75 as:

$$\eta_{sp} = \frac{\eta}{\eta_0} - 1 = \frac{4\Delta p}{IP - 2\Delta p}, \quad (3)$$

where $\eta_{sp}$ is the specific viscosity, $\eta$ is the viscosity of the sample under test, $\eta_0$ is the solvent viscosity, $\Delta p$ is the measurement of the transducer 74, and IP is the measurement of the transducer 75.

Mathematical consideration is now given in order to evaluate whether the process of thermal tuning, or the effect of connecting non-identical flow impedances in the bridge arms, affects the accuracy of the resulting measurement. It can be easily shown that when solvent is flowing through all arms of the temperature regulated bridge 50, the ratio of the pressures measured in the two transducers 74 and 75 is given by:

$$\frac{\Delta p}{IP} = \frac{1}{1 + \frac{R_{52}}{R_{54}}} - \frac{1}{1 + \frac{\eta_0}{\eta_T}\frac{R_{64}}{R_{66}}}, \quad (4)$$

where $\eta_T$ is the viscosity of the solvent passing through the thermally controlled tuning arm $R_{66}$.

When the bridge 50 is balanced, $\Delta p=0$, which implies the corresponding balance condition:

$$\frac{R_{52}}{R_{54}} = \frac{\eta_0}{\eta_T} \frac{R_{64}}{R_{66}}, \qquad (5)$$

where the ratio $R_{52}/R_{54} \equiv y$, for purposes of simplification. Clearly when the temperature of the thermally controlled stage containing $R_{66}$ is identical to the rest of the bridge (i.e. $\theta_T = \eta_0$), this reduces to the traditional Wheatstone bridge balance condition. When the sample with viscosity $\theta_s$ is introduced to the viscometer, it passes through arms $R_{64}$, $R_{52}$, and $R_{54}$. However, since the delay reservoir 72 is filled with solvent, $R_{66}$ is supplied with solvent at the control temperature with viscosity $\eta_T$. Therefore the ratio of the transducer pressures is now given by:

$$\frac{\Delta p}{IP} = \frac{1}{1 + \frac{R_{52}}{R_{54}}} - \frac{1}{1 + \frac{\eta_s}{\eta_T} \frac{R_{64}}{R_{66}}}. \qquad (6)$$

In terms of y, the Equation (6) is simplified to:

$$\frac{\Delta p}{IP} = \frac{1}{1 + y} - \frac{1}{1 + \frac{\eta_s}{\eta_0} y}. \qquad (7)$$

This simplified Equation (7) can be solved for the specific viscosity, defined as $\eta_{sp} \equiv \eta_s/\eta_0 - 1$, as:

$$\eta_{sp} = \frac{\Delta p (1+y)^2}{[IP - dp(1+y)]y}. \qquad (8)$$

Accordingly, if the y parameter is known, precise measurements of the specific viscosity can be made. However, because no manufacturing process is perfect, the y parameter is typically not known a priori and is difficult to measure accurately. Assume that the resistances $R_{52} \sim R_{54}$ are nearly equal so that one may write $y = 1 + \epsilon$, were $\epsilon$ is a small parameter. In this case, the Equation (8) can be rewritten as:

$$\eta_{sp} = \frac{4\Delta p}{IP - 2\Delta p} + \frac{4\Delta p^2}{(IP - 2\Delta p)^2} \epsilon + O(\epsilon^2). \qquad (9)$$

This is a fundamental result. Alternatively, this same result may be written as $$\frac{\eta_{sp}(\epsilon)}{\eta_{sp}(\epsilon=0)} = 1 + \frac{\epsilon}{4} \eta_{sp}(\epsilon=0) + O(\epsilon^2), \qquad (10)$$

where $\eta_{sp}(\epsilon=0)$ is the true value of the specific viscosity that would be measured by an ideal bridge. This result implies that if the $\epsilon$ correction for a non-ideal bridge is neglected, only a percentage error in the order of $\epsilon \eta_{sp}/4$ is incurred.

Since the range of specific viscosities that are measured by online bridge viscometers is typically much less than 1 and the bridges are typically manufactured so that $\epsilon$ is much less than 1, this error is of a second order in magnitude and can safely be neglected. However, this analysis assumes that the bridge 50 has been thermally balanced in the manner described above.

The presence of a thermally controlled tuning stage like that shown in FIG. 2 also allows a new method of operation of the differential viscometer. Typically, the bridge is tuned before the sample has been introduced to the instrument when only solvent is flowing though both sides of the bridge. The temperatures are then held constant when the sample is introduced. The specific viscosity is measured from the imbalance pressure as described earlier in Equation (3). However, by virtue of the present improvement, it is now possible to instead adjust the temperature of the tuning element (e.g., capillary 18) of the bridge to keep the bridge in balance while the sample elutes. The temperature is now adjusted to servo the differential pressure transducer 74 to zero without going into saturation. In this case, the temperature difference between the bridge and the tuning length becomes a measure of the specific viscosity represented by:

$$\eta_{sp} = \frac{1}{\eta_0} \frac{d\eta}{dT}\bigg|_{T_0} (T - T_0) + O(T - T_0)^2, \qquad (11)$$

where, $T_0$ is the original tuning temperature, T is the time dependent temperature required to maintain $\Delta p = 0$. This method requires the temperature control system to be able to change the temperature of the tuning capillary 18 rapidly enough to always keep $\Delta p = 0$. It also requires a priori knowledge of a new parameter $$\frac{1}{\eta_0} \frac{d\eta}{dT}\bigg|_{T_0}.$$

It is to be recognized that it is within the scope of this improvement to cool (rather than heat) the core 20 within the housing 22 to increase the pressure drop of the capillary 18 and the total pressure of the arm 10 so as to trim in the balance of the bridge. In this case, a Peltier thermoelectric device, rather than the heater 24 of FIG. 2, will be located in close thermal contact with the capillary 18 and/or the core 20 to provide thermal regulation of the capillary 18 in fluid arm 10 relative to the other bridge arms. More particularly, and turning to FIG. 3 of the drawings, there is shown the addition of a conventional Peltier thermoelectric device 23, one side of which lies in close thermal contact with the thermally conductive core 20 around which the thermally tuned capillary 18 is wound within the thermally insulated housing 22. The opposite side of the Peltier device 23 is coupled to a heat sink 24 located outside housing 22 to vent excess heat to the atmosphere.

Figure 3:
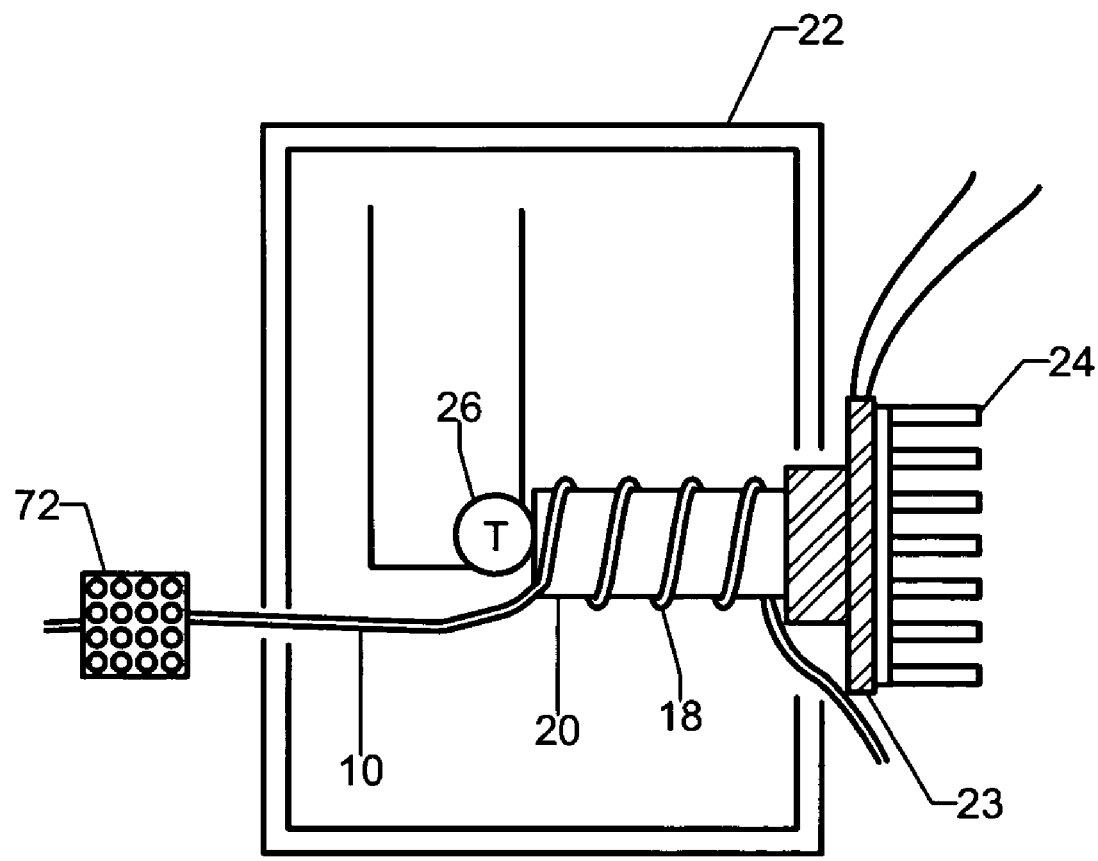
FIG. 3 shows details of another thermally controlled stage that is added to one arm of the bridge of FIG. 1 and that includes a Peltier thermoelectric device to allow either heating or cooling.

Such a Peltier device 23 as that shown in FIG. 3 can also heat as well as cool the thermally controlled capillary 18. The additional benefit that a Peltier device confers is the ability to servo the thermally controlled capillary 18 to nearly the same temperature as the rest of the bridge, whereas the heater 24 of FIG. 2 can only regulate the temperature of the controlled capillary at a higher temperature than the rest of the bridge. The heater method therefore requires that the controlled capillary have an initially higher flow impedance than would otherwise be required for balancing, so that the heater may lower the resistance to the correct value.

Figure 4:
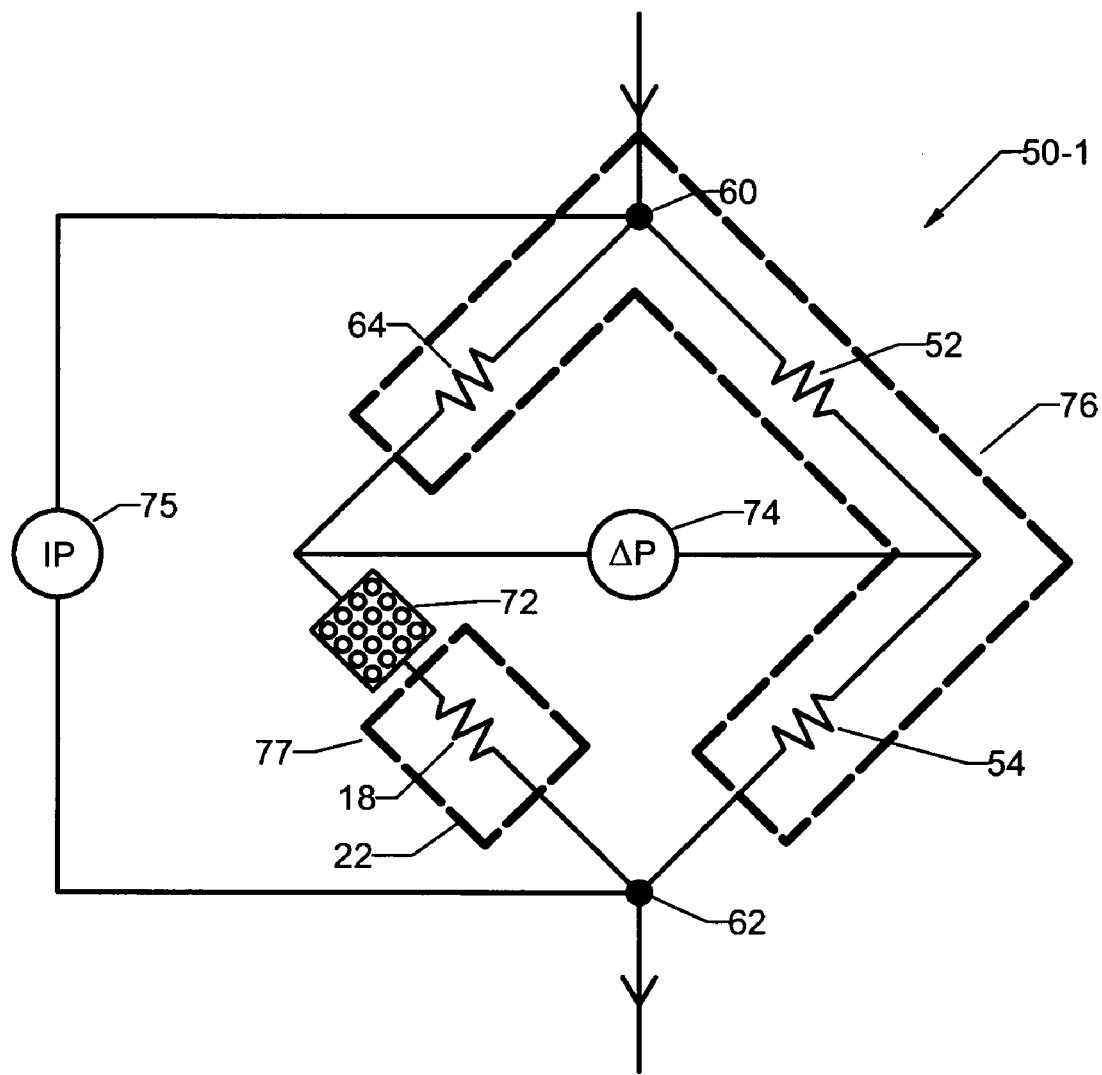
FIG. 4 shows an alternate embodiment where several arms of the bridge of FIG. 1 are independently thermally controlled.

In the bridge balancing embodiments shown in FIGS. 2 and 3, a single fluid arm 10 of the bridge 50 (of FIG. 1) containing the fluid sample delay volume 72 is thermally controlled. In this case, a thermally controlled stage including a thermally tuned capillary 18 is connected in the arm 10 and isolated from the other arms within housing 22. However, it is also within the scope of this invention to thermally control several arms of a bridge 50-1 in the manner to be described while referring to FIG. 4 of the drawings. That is to say, and as an alternate embodiment of this invention, other thermally tuned capillaries (designated 52, and 64 in FIG. 4) having equivalent flow impedances can be connected into respective other fluid arms of the bridge 50-1 and temperature regulated in the same manner as that described above. In this case, there will be two independently controlled thermal stages. A first independently controlled stage includes capillaries 52, 54 and 64 located in a thermally controlled space 76. The second independently controlled stage includes the aforementioned capillary 18 located in thermally controlled space 22. The relevant control parameter is the temperature difference between the two stages 22 and 76. In this manner, the bridge stability is improved inasmuch as the flow impedances of capillaries 52, 54 and 64 are not subject to changes in ambient temperature.

Lastly, although one may thermally regulate an entire bridge arm, it is also possible to thermally regulate a section of one of the bridge arms. The remainder of the control arms is thermally anchored to the other bridge arms. In this manner, the effect of thermal noise which may be inadvertently injected into the control stage is minimized, but the analysis above is unchanged.

I claim:

1. A capillary bridge viscometer having a bridge for receiving a solvent and containing a first pair of series connected fluid tubing arms and a second pair of series connected fluid tubing arms, said second pair of fluid tubing arms connected in parallel with said first pair of series connected fluid tubing arms between fluid supply and fluid discharge ports, and a thermally controlled stage connected into one of said fluid tubing arms by which to balance said bridge, said thermally controlled stage comprising a thermally conductive capillary tubing portion being wound around a thermally conductive core and having a flow impedance, and means to change the temperature of said capillary tubing portion to correspondingly change the flow impedance thereof until the differential pressure across said bridge is 0.

2. The capillary bridge viscometer recited in claim 1, wherein said capillary tubing portion of said thermally controlled stage includes a series of windings that are wound around said thermally conductive core.

3. The capillary bridge viscometer recited in claim 1, also having a fluid sample delay volume connected in the one of said fluid tubing arms in which said thermally controlled stage is connected, said capillary tubing portion of said thermally controlled stage located downstream from said fluid sample delay volume and closer to said discharge port than to said supply port.

4. The capillary bridge viscometer recited in claim 1, wherein the means to change the temperature of said capillary tubing portion of said thermally controlled stage to correspondingly change the flow impedance thereof is a heater located in proximity to said capillary tubing portion for heating said capillary tubing portion.

5. The capillary bridge viscometer recited in claim 4, wherein said heater is a Peltier thermoelectric device located in close proximity to said capillary tubing portion wound around said thermally conductive core.

6. The capillary bridge viscometer recited in claim 4, wherein said heater is a resistance heater, the power to said resistance heater being adjusted to vary the heat generated by said heater and to correspondingly control the flow impedance of said capillary tubing portion in response to the heat generated by said heater.

7. The cap lary bridge viscometer recited in claim 4, wherein said thermally controlled stage rther comprises a thermally insulated housing to enclose said capillary tubing portion w und around said thermally conductive core and said heater located in close proximity to said capillary tubing portion.

8. The capillary bridge viscometer recited in claim 7, wherein said thermally controlled stage further comprises a temperature probe located within said thermally insulated housing to measure the temperature of said capillary tubing portion wound around said thermally conductive core.

9. For a capillary bridge viscometer having a bridge for receiving a solvent and fluid samples to be analyzed and containing a first pair of series connected fluid tubing arms and a second pair of series connected fluid tubing arms, said second pair of fluid tubing arms connected in parallel with said first pair of series connected fluid tubing arms between fluid supply and fluid discharge ports, a method for balancing said bridge including the step of regulating the temperature of at least one fluid tubing arm of said first and second pairs of fluid tubing arms relative to the other fluid tubing arms until the differential pressure across said bridge is 0.

10. The method for balancing a bridge as recited in claim 9, including the additional steps of regulating the temperature of said one fluid tubing arm after the solvent has first been supplied to the first and second pairs of parallel connected fluid tubing arms and said bridge has stabilized, and then holding the temperature of said at least one fluid tubing arm constant while the fluid samples to be analyzed are introduced to said bridge.

11. The method for balancing a bridge as recited in claim 9, including the additional step of rebalancing the bridge of said capillary bridge viscometer by continuously regulating the temperature of said at least one fluid tubing arm as the fluid samples to be analyzed flow through said viscometer, such that the temperature required to rebalance said bridge providing a measurement of the specific viscosity of the samples.

12. The method for balancing a bridge as recited in claim 9, including the additional step of regulating the temperature of the other fluid tubing arms of said first and second pairs of fluid tubing arms independently of the temperature of said one fluid tubing arm.

13. The method for balancing a bridge as recited in claim 12, including the additional steps of connecting into said one fluid tubing arm a first thermally conductive capillary tubing portion having a flow impedance, connecting into said other fluid tubing arms respective other thermally conductive capillary tubing portions having flow impedances, and providing thermal isolation of said first thermally conductive capillary tubing portion from said other thermally conductive capillary tubing portions.

14. The method for balancing a bridge recited in claim 9, including the additional steps of regulating the temperature of said one fluid tubing arm by connecting into said one fluid tubing arm a thermally conductive capillary tubing portion having a flow impedance and heating or cooling said capillary tubing portion to cause a corresponding change in the flow impedance thereof.

15. The method for balancing a bridge recited in claim 14, including the additional step of isolating said thermally conductive capillary tubing portion connected in said one fluid tubing arm from the other fluid tubing arms of said bridge by locating said capillary tubing portion in a thermally insulated housing.

16. The method for balancing a bridge recited in claim 14, including the additional step of heating said thermally conductive capillary tubing portion by means of a heater located in close proximity thereto.

17. The method for balancing a bridge recited in claim 14, including the additional step of heating or cooling said thermally conductive capillary tubing portion by means of a Peltier thermoelectric device located in close proximity thereto.

18. The method for balancing a bridge recited in claim 14, including the additional steps of attaching said thermally conductive capillary tubing portion to a thermally conductive core and heating or cooling said thermally conductive core for heating or cooling said capillary tubing portion.

19. The method for balancing a bridge recited in claim 14, including the additional step of winding said thermally conductive capillary tubing portion around said thermally conductive core.

20. The method for balancing a bridge recited in claim 14, including the additional step of monitoring the temperature of said thermally conductive capillary tubing portion.

21. The method for balancing a bridge recited recited in claim 20, including the additional step of maintaining the temperature of said thermally conductive capillary tubing portion constant once the differential pressure across said bridge is 0.

* * * * *